US00PP24228P2

(12) United States Plant Patent
Robb

(10) Patent No.: US PP24,228 P2
(45) Date of Patent: Feb. 11, 2014

(54) ***GARDENIA* PLANT NAMED 'STARLIGHT'**

(50) Latin Name: *Gardenia augusta*
Varietal Denomination: Starlight

(75) Inventor: John Robb, Kariong (AU)

(73) Assignee: The Paradise Seed Company Pty. Ltd., Kariong, NSW (AU)

( * ) Notice: Subject to any disclaimer, the term of this patent is extended or adjusted under 35 U.S.C. 154(b) by 66 days.

(21) Appl. No.: 13/506,507

(22) Filed: Apr. 23, 2012

(51) Int. Cl.
*A01H 5/00* (2006.01)

(52) U.S. Cl.
USPC ..... Plt./255

(58) Field of Classification Search
USPC ..... Plt./255
See application file for complete search history.

*Primary Examiner* — Annette Para
(74) *Attorney, Agent, or Firm* — C. A. Whealy

(57) ABSTRACT

A new and distinct cultivar of *Gardenia* plant named 'Starlight', characterized by its compact, upright to outwardly spreading and rounded plant habit; moderately vigorous growth habit; freely branching and flowering plant habit; long leaves; numerous large single white-colored flowers; and good garden performance.

2 Drawing Sheets

Botanical designation: *Gardenia augusta.*
Cultivar denomination: 'STARLIGHT'.

BACKGROUND OF THE INVENTION

The present invention relates to a new and distinct cultivar of *Gardenia* plant, botanically known as *Gardenia augusta* and hereinafter referred to by the name 'Starlight'.

The new *Gardenia* plant is a product of a planned breeding program conducted by the Inventor in Kulnura, New South Wales, Australia. The objective of the breeding program is to develop new compact and freely branching *Gardenia* plants with attractive flowers.

The new *Gardenia* plant originated from an open-pollination in December, 2007 in Kulnura, New South Wales, Australia of *Gardenia augusta* 'Radicans', not patented, as the female, or seed, parent with an unknown selection of *Gardenia augusta* as the male, or pollen, parent. The new *Gardenia* plant was discovered and selected by the Inventor as a single flowering plant within the progeny of the stated open-pollination in a controlled environment in Kulnura, New South Wales, Australia in 2010.

Asexual reproduction of the new *Gardenia* plant by vegetative cuttings in a controlled greenhouse environment in Kulnura, New South Wales, Australia since 2010 has shown that the unique features of this new *Gardenia* plant are stable and reproduced true to type in successive generations.

SUMMARY OF THE INVENTION

Plants of the new *Gardenia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Starlight'. These characteristics in combination distinguish 'Starlight' as a new and distinct *Gardenia* plant:

1. Compact, upright to outwardly spreading and rounded plant habit.
2. Moderately vigorous growth habit.
3. Freely branching and flowering plant habit.
4. Long leaves.
5. Numerous large single white-colored flowers.
6. Good garden performance.

Plants of the new *Gardenia* can be compared to plants of the female parent, 'Radicans'. Plants of the new *Gardenia* differ primarily from plants of 'Radicans' in the following characteristics:

1. Plants of the new *Gardenia* have longer leaves than plants of 'Radicans'.
2. Plants of the new *Gardenia* have single flowers whereas plants of 'Radicans' have semi-double flowers.

Plants of the new *Gardenia* can also be compared to plants of *Gardenia* 'Grandiflora Star', not patented. In side-by-side comparisons conducted in Kulnura, New South Wales, Australia, plants of the new *Gardenia* and 'Grandiflora Star' differed primarily in the following characteristics:

1. Plants of the new *Gardenia* had longer leaves than plants of 'Grandiflora Star'.
2. Plants of the new *Gardenia* had larger flowers than plants of 'Grandiflora Star'.

BRIEF DESCRIPTION OF THE PHOTOGRAPHS

The accompanying colored photographs illustrate the overall appearance of the new *Gardenia* plant showing the colors as true as it is reasonably possible to obtain in colored reproductions of this type. Colors in the photographs may differ slightly from the color values cited in the detailed botanical description which accurately describe the colors of the new *Gardenia* plant.

The photograph on the first sheet comprises a side perspective view of a typical flowering plant of 'Starlight' grown in a container.

The photograph on the second sheet is a close-up view of a typical opened flower of 'Starlight'.

DETAILED BOTANICAL DESCRIPTION

The aforementioned photographs and following observations, measurements and values describe plants grown during the summer in 25-cm containers in a polyethylene-covered greenhouse in Cranbourne, New South Wales, Australia and under cultural practices typical of commercial *Gardenia* production. During the production of the plants, day temperatures ranged from 10° C. to 40° C., night temperatures ranged from 4° C. to 28° C. and light levels ranged from 5,000 to 9,000 foot-candles. Plants were 18 months old when the photographs and the description were taken. In the following description, color references are made to The Royal Horticultural Society Colour Chart, Fifth Edition, except where general terms of ordinary dictionary significance are used.

Botanical classification: *Gardenia augusta* 'Starlight'.

Parentage:

*Female, or seed, parent.*—*Gardenia augusta* 'Radicans', not patented.

*Male, or pollen, parent*.—Unknown selection of *Gardenia augusta*, not patented.

Propagation:

*Type*.—By vegetative cuttings.

*Time to initiate roots, summer*.—About 30 to 50 days at 22° C.

*Time to initiate roots, winter*.—About 40 to 60 days at 22° C.

*Time to produce a rooted young plant, summer*.—About 84 days at 15° C. to 40° C.

*Time to produce a rooted young plant, summer*.—About 100 days at 0° C. to 12° C.

*Root description*.—Medium in thickness, fleshy; white to brown in color.

*Rooting habit*.—Moderately freely branching; medium density.

Plant description:

*Plant and growth habit*.—Compact, upright to outwardly spreading and rounded plant habit; freely branching habit with numerous lateral branches developing per plant; pinching enhances lateral branch development; moderately vigorous growth habit.

*Plant height*.—About 50 cm to 70 cm.

*Plant diameter*.—About 50 cm to 70 cm.

Lateral branch description:

*Length*.—About 20 cm to 30 cm.

*Diameter*.—About 5 mm to 10 mm.

*Internode length*.—About 3.2 cm.

*Strength*.—Strong.

*Aspect*.—Upright to outwardly spreading.

*Texture*.—Smooth, glabrous.

*Color*.—Brown.

Foliage description:

*Arrangement*.—Alternate, simple; sessile.

*Length*.—About 10.7 cm.

*Width*.—About 1.9 cm.

*Shape*.—Narrowly elliptic.

*Apex*.—Acute.

*Base*.—Short attenuate to cuneate.

*Margin*.—Entire.

*Texture, upper and lower surfaces*.—Smooth, glabrous.

*Venation pattern*.—Pinnate.

*Color*.—Developing leaves, upper and lower surfaces: Close to 144C. Fully expanded leaves, upper surface: Close to 147C; venation, close to 144C. Fully expanded leaves, lower surface: Close to 144C; venation, slightly darker than 144C.

Flower description:

*Flower arrangement and habit*.—Single rotate flowers arising from upper leaf axils; freely flowering habit with usually about 50 flowers developing per plant; flowers face mostly upright.

*Fragrance*.—Strongly fragrant; pleasant.

*Natural flowering season*.—Plants of the new *Gardenia* flower continuously for about two to three weeks during the spring and summer in Australia; flowers not persistent.

*Flower diameter*.—About 7 cm.

*Flower length* (*depth*).—About 5 cm to 7 cm.

*Flower buds*.—Length: About 5 cm to 6 cm. Diameter: About 1 cm to 1.5 cm. Shape: Roughly spatulate. Color: Lighter than 144C.

*Petals*.—Quantity and arrangement: About six in a single whorl. Length: About 4 cm to 6 cm. Width: About 2 cm to 3 cm. Shape: Oblong to obovate. Apex: Rounded. Base: Attenuate. Margin: Entire; with development, revolute. Texture, upper and lower surfaces: Smooth, glabrous. Color: When opening, upper surface: Close to 158D. When opening, lower surface: Close to 158D and 144B. Fully opened, upper and lower surfaces: Close to 155B.

*Sepals*.—Arrangement: Star-shaped calyx with six sepals fused at the base. Length: About 2 cm. Width: About 1 mm to 4 mm. Shape: Lanceolate. Apex: Acuminate. Margin: Entire. Texture, upper and lower surfaces: Smooth, glabrous. Color, upper and lower surfaces: Close to 144B.

*Peduncles*.—Length: About 1 cm. Diameter: About 3 mm to 5 mm. Angle: Upright. Strength: Strong. Texture: Smooth, glabrous. Color: Close to 143A.

*Reproductive organs*.—Stamens: Quantity: Six per flower. Anther length: About 1 cm. Anther shape: Lanceolate. Anther color: Close to 199C. Pollen amount: Abundant. Pollen color: Close to 13C.

*Pistils*.—Quantity and arrangement: One per flower irregularly divided into two segments. Style length: About 3.5 cm to 4.5 cm. Style color: White. Stigma shape: Elliptic. Stigma color: Close to 10C.

*Seeds and fruits*.—Seed and fruit development have not been observed on plants of the new *Gardenia*.

Garden performance: Plants of the new *Gardenia* have been observed to have good garden performance and to tolerate wind and temperatures ranging from about 1° C. to about 40° C.

Pathogen & pest resistance: Plants of the new *Gardenia* have not been observed to be resistant to pests and pathogens common to *Gardenia* plants.

It is claimed:

1. A new and distinct *Gardenia* plant named 'Starlight' as illustrated and described.

* * * * *

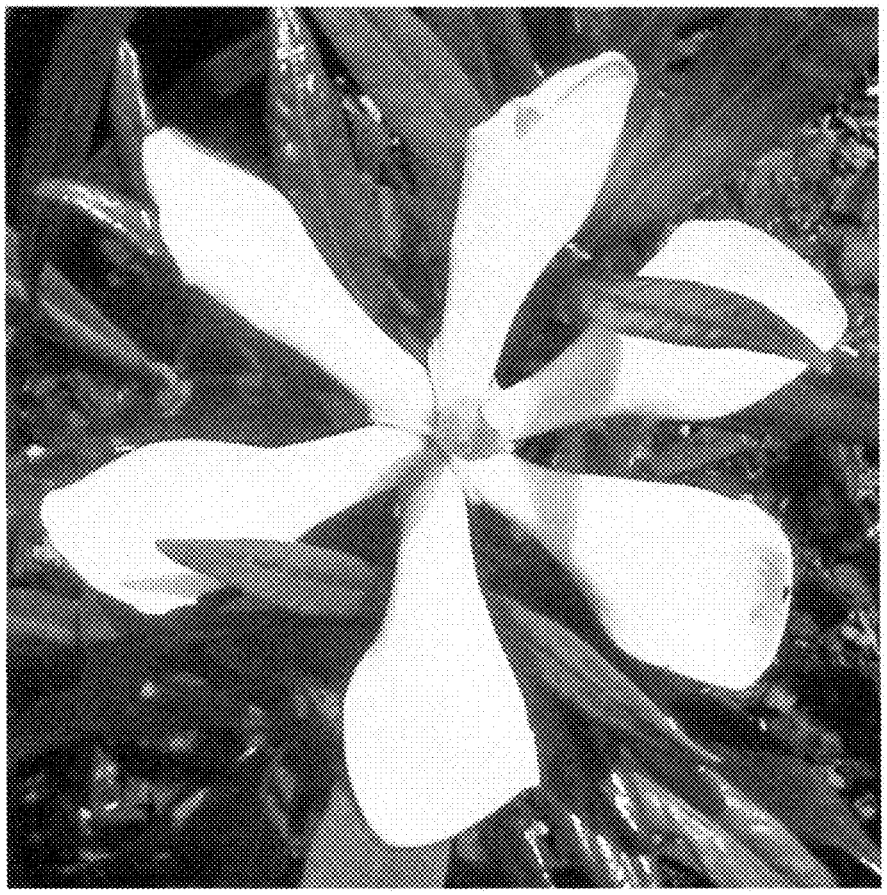

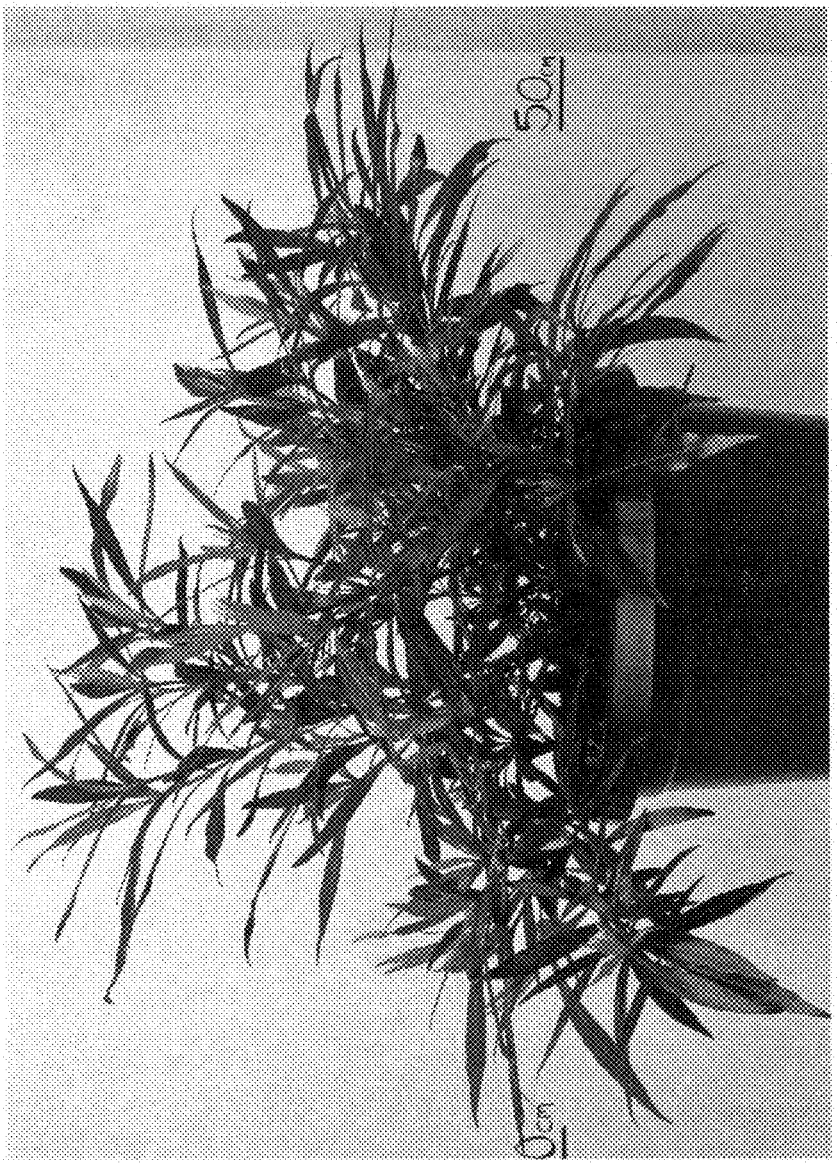
50cm
15cm